(12) United States Patent
Rajan et al.

(10) Patent No.: US 8,716,471 B2
(45) Date of Patent: May 6, 2014

(54) PROCESS FOR THE PREPARATION OF TETRAZINE DERIVATIVES

(75) Inventors: Gupte Rajan, Maharashtra (IN); Chaturvedi Rohit, Maharashtra (IN); Baviskar Pravin, Maharashtra (IN)

(73) Assignee: Reliance Life Sciences Pvt. Ltd., Mumbai (IN)

( * ) Notice: Subject to any disclaimer, the term of this patent is extended or adjusted under 35 U.S.C. 154(b) by 171 days.

(21) Appl. No.: 13/130,826

(22) PCT Filed: Nov. 24, 2009

(86) PCT No.: PCT/IN2009/000681
§ 371 (c)(1),
(2), (4) Date: May 24, 2011

(87) PCT Pub. No.: WO2010/058430
PCT Pub. Date: May 27, 2010

(65) Prior Publication Data
US 2011/0230658 A1  Sep. 22, 2011

(30) Foreign Application Priority Data

Nov. 24, 2008 (IN) .......................... 2475/MUM/2008

(51) Int. Cl.
C07D 487/04 (2006.01)
A61K 31/395 (2006.01)
A61P 35/00 (2006.01)

(52) U.S. Cl.
USPC ...................................... 544/179; 548/326.5

(58) Field of Classification Search
USPC ...................................... 544/179; 548/326.5
See application file for complete search history.

(56) References Cited

U.S. PATENT DOCUMENTS

| 4,082,787 A | 4/1978 | Bassett et al. |
| 4,141,913 A | 2/1979 | Schwartzman et al. |
| 4,207,251 A | 6/1980 | Heyboer |
| 4,255,350 A | 3/1981 | Aliev et al. |
| 4,391,758 A | 7/1983 | Spaziante et al. |
| 4,620,030 A | 10/1986 | Heinsohn et al. |
| 5,260,291 A | 11/1993 | Lunt et al. |
| 2007/0225496 A1 | 9/2007 | Palle et al. |

FOREIGN PATENT DOCUMENTS

JP          56/100751 A      8/1981

OTHER PUBLICATIONS

Huai You Wang, et al., "Determination of methyl isocyanate in air by fluorimetry", Analyst, vol. 124, 1999, pp. 1327-1330.
Shealy, Y. Fulmer, et al., "Synthesis of Potential Anticancer Agents. XXIX. 5-Diazoimidazole-4-carboxamide and 5-Diazo-υ-triazole-4-carboxamide1,2", Journal of Organic Chemistry, vol. 26, Jul. 1961, pp. 2396-2401.
Beligny, Samuel, "International Search Report", for PCT/IN2009/000681 as mailed May 6, 2010, 3 pages.

*Primary Examiner* — Venkataraman Balasubramanian
(74) *Attorney, Agent, or Firm* — Winstead PC

(57) ABSTRACT

The present invention provides a process for the preparation of a tetrazine derivative of formula (I), or a pharmaceutically acceptable salt thereof wherein $R_1$ represents a hydrogen atom, a straight or branched $C_1$-$C_6$ alkyl group, $C_2$-$C_6$ alkenyl group or $C_2$-$C_6$ alkynyl group, which $C_1$-$C_6$ alkyl group, $C_2$-$C_6$ alkenyl group and $C_2$-$C_6$ alkynyl group is unsubstituted or substituted with 1, 2 or 3 substituents selected from halogen atoms, straight or branched $C_1$-$C_4$ alkoxy groups, $C_1$-$C_4$ alkylthio groups, $C_1$-$C_4$ alkylsulphinyl groups, $C_1$-$C_4$ alkylsulphonyl groups and phenyl groups, which phenyl groups are unsubstituted or substituted with one or more substituents selected from $C_1$-$C_4$ alkyl groups, $C_1$-$C_4$ alkoxy groups and nitro groups; or $R_1$ represents a $C_3$-$C_8$ cycloalkyl group; and $R_2$ represents a group of formula —(C═O)NR$_3$R$_4$, wherein $R_3$ and $R_4$ are independently selected from hydrogen atoms, $C_1$-$C_4$ alkyl groups, $C_2$-$C_4$ alkenyl groups and $C_3$-$C_8$ cycloalkyl groups, which process comprises: i) providing a compound N of formula (III), wherein $R_1$ is as defined; $R_1$—N═C═O ii) absorbing the compound of formula (III) into a solvent to obtain a solution of the compound of formula (III); iii) adding to the thus obtained solution a compound of formula (II), to obtain a compound of formula (I), as defined above, wherein $R_2$ is as defined above; iv) decomposing any excess compound of formula (III) remaining by addition of water; and v) optionally salifying the thus obtained compound with a pharmaceutically acceptable acid, or base.

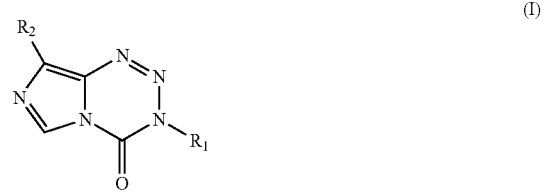

(I)

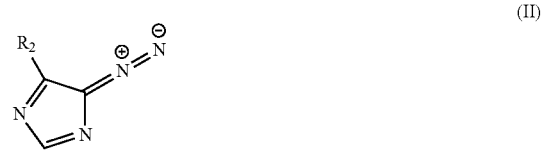

(II)

7 Claims, No Drawings

PROCESS FOR THE PREPARATION OF TETRAZINE DERIVATIVES

CROSS-REFERENCE TO RELATED PATENT APPLICATIONS

The present application claims priority to Indian Provisional Patent Application No. 2475/MUM/2008, filed Nov. 24, 2009, which is entirely incorporated herein by reference.

TECHNICAL FIELD

The present invention relates to an improved process for the preparation of tetrazine derivatives. In particular, the present invention relates to a process for the preparation of industrially feasible temozolomide and its derivatives whereby harmful isocyanates, in particular MIC, are safely handled by absorbing them in an appropriately chosen solvent.

BACKGROUND

Temozolomide (TMZ) is an imidazotetrazine derivative that exhibits anti tumor activity. TMZ's activity in vivo is attributed to its potent methylating activity. TMZ is available under the brand name TEMODAR in the form of capsules containing 5 mg, 20 mg, 100 mg or 250 mg of TMZ. TMZ is indicated in the treatment of refractory anaplastic astrocytoma, a form of brain tumour, glioblastoma multiforme and metastatic melanoma.

TMZ is the abbreviation for a compound having the chemical structure 3,4-dihydro-3-methyl-4-oxoimidazo[5,1-d]1,2,3,5-tetrazine-8-carboxamide or 3-methyl-8-amino carbonyl-imidazo[5,1-d]-1,2,3,5-tetrazin-4(3H)-one. It has the following structure.

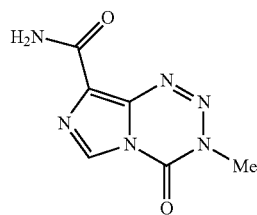 [SMILES: Cn1nnc2c(C(N)=O)ncn2c1=O]

U.S. Pat. No. 5,260,291, the entirety of which is incorporated herein by reference, describes TMZ and its derivatives. Also described is a process for the preparation of TMZ and its derivatives involving condensation of 5-diazo-5H-imidazole-4 carboxamide (and related compounds) with isocyanates. However, the process described is very slow, involving reaction times of up to 3 weeks. The process described is also hazardous as it involves handling isocyanates, particularly methyl isocyanate (MIC) either in the gaseous or liquid state.

In general, isocyanates are harmful to animals: they are toxic and exposure is known to cause asthma in humans. In particular, methyl isocyanate (MIC) has the structure $CH_3-N=C=O$ and is a volatile (Bp=39.1° C.) colourless liquid. MIC is extremely toxic to animal life and can cause damage by inhalation, contact and ingestion even at concentrations as low as 0.4 ppm.

Due to its relatively low boiling point, MIC vaporises easily which can lead to escape of this reagent into the environment, where it can damage animal life. MIC in the liquid state polymerises readily in an exothermic reaction. When traces of acids, bases or metals are present, the polymerization can occur in an explosive way. These factors combine to make isocyanates, particularly MIC, very difficult to handle safely, particularly on an industrial scale.

US 2007/0225496, the entirety of which is incorporated herein by reference, describes a process for the preparation of TMZ comprising pyrrolysing N'-Methyl-N,N-diphenyl urea to form MIC vapour and slowly condensing the MIC vapour into a reservoir of a solution of 5-diazo-5H-imidazole-4-carboxamide in dimethyl sulphoxide (DMSO). A yield of crude temozolomide of 68.6% is reported. During filtration of the crude temozolomide produced in this process, excess MIC vapors may be released to the atmosphere.

It has now surprisingly been found that the compounds described in U.S. Pat. No. 5,260,291 can be prepared by a new process developed under the present invention that avoids many of the problems encountered in the prior art. The US 2007/0225496 patent describes the process for the preparation of TMZ comprises of pyrrolysing N'-Methyl-N,N-diphenyl urea to form MIC vapour which slowly condenses the MIC vapour into a reservoir of a solution of 5-diazo-5H-imidazole-4-carboxamide in dimethyl sulphoxide (DMSO) whereby excess of MIC vapors may be released to the atmosphere. The inventors of the present invention have worked around curbing the MIC vapors in the atmosphere and have come out with a unique process whereby TMZ is prepared by using a reservoir of a solution of an isocyanate, particularly MIC, in a solvent followed by subsequent addition of 5-diazo-5H-imidazole-4-carboxamide, or a derivative thereof. By the present process MIC vapors are not released in the atmosphere, in fact they are absorbed into a solvent. The present process is thus found to be more industrially feasible as compared to the conventional processes for the preparation of TMZ.

The process of the present invention enables a faster reaction, an improvement in yield and/or an improved purity of the TMZ derivative produced. Further, the process of the present invention allows any excess isocyanate to be destroyed in situ with aqueous acid, thus minimising the risk of release of isocyanate to the atmosphere.

SUMMARY OF INVENTION

The present invention therefore provides a process for the preparation of a tetrazine derivative of formula (I), or a pharmaceutically acceptable salt thereof

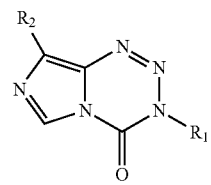

I wherein
  $R_1$ represents a hydrogen atom, a straight or branched $C_1$-$C_6$ alkyl group, $C_2$-$C_6$ alkenyl group or $C_2$-$C_6$ alkynyl group, which $C_1$-$C_6$ alkyl group, $C_2$-$C_6$ alkenyl group and $C_2$-$C_6$ alkynyl group is unsubstituted or substituted with 1, 2 or 3 substituents selected from halogen atoms, straight or branched $C_1$-$C_4$ alkoxy groups, $C_1$-$C_4$ alkylthio groups, $C_1$-$C_4$ alkylsulphinyl groups, $C_1$-$C_4$ alkylsulphonyl groups and phenyl groups, which phenyl groups are unsubstituted or substituted with one or more substituents selected from $C_1$-$C_4$ alkyl groups, $C_1$-$C_4$ alkoxy groups and nitro groups; or $R_1$ represents a $C_3$-$C_8$ cycloalkyl group; and $R_2$ represents a group of formula —(C=O)$NR_3R_4$, wherein $R_3$ and $R_4$ are independently selected from hydrogen atoms, $C_1$-$C_4$ alkyl groups, $C_2$-$C_4$ alkenyl groups and $C_3$-$C_8$ cycloalkyl groups, which process comprises:

i) providing a compound of formula (III), wherein $R_1$ is as defined above;

$$R_1-N=C=O \quad \text{III}$$

ii) absorbing the compound of formula (III) into a solvent to obtain a solution of the compound of formula (III);
iii) adding to the thus obtained solution a compound of formula (II), to obtain a compound of formula (I), as defined above,

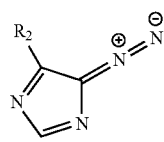

wherein $R_2$ is as defined above;
iv) decomposing any excess compound of formula (III) remaining by addition of water; and
v) optionally salifying the thus obtained compound with a pharmaceutically acceptable acid, or base.

The present invention further provides a compound of formula (I) obtained by the process of the present invention.

The present invention further provides use of a composition comprising a compound of formula (III), as defined herein, absorbed in a solvent, as defined herein, in the synthesis of a compound of formula (I), as defined herein.

In a preferred embodiment of the invention, the solvent used in step (iii) is dioxane. Use of a dioxane solvent leads to a faster formation of tetrazine derivatives compared with other non-polar solvents and other aprotic polar solvents.

DETAILED DESCRIPTION OF THE INVENTION

Scheme 1 below shows a process of the invention, in which the compound of formula (I) is temozolomide.

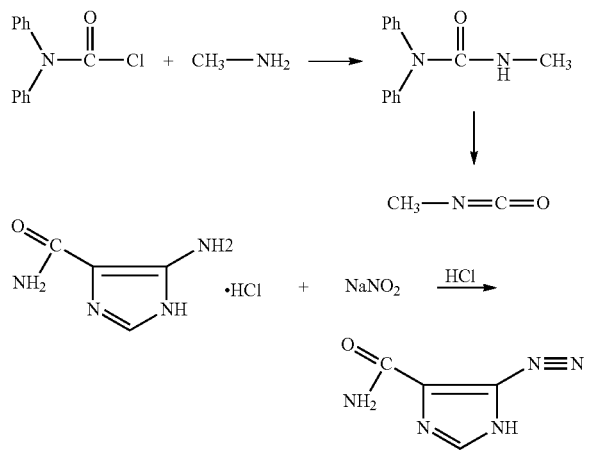

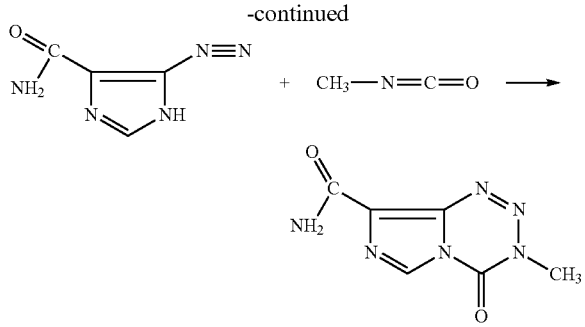

TEMOZOLAMIDE

"MIC" as used herein refers to methyl isocyanate.
"TMZ" as used herein refers to temozolomide including all polymorphs, solvates, esters and salts thereof.

As used herein, the term halogen atom refers to chlorine, fluorine, bromine or iodine atoms typically a fluorine, chlorine or bromine atom, most preferably chlorine or fluorine. The term halo when used as a prefix has the same meaning.

As used herein, the term $C_1$-$C_6$ alkyl includes both saturated straight chain and branched alkyl groups. Examples of $C_1$-$C_6$ alkyl groups include methyl, ethyl, propyl, isopropyl, butyl, isobutyl, tert-butyl, pentyl and hexyl. Preferably, the $C_1$-$C_6$ alkyl group is a $C_{1-4}$ alkyl group, more preferably a $C_{1-3}$ alkyl group.

As used herein, a $C_1$-$C_4$ alkoxy group is a said $C_1$-$C_4$ alkyl group, for example a $C_1$-$C_2$ alkyl group, which is attached to an oxygen atom. Preferably said $C_1$-$C_4$ alkoxy group is a methoxy group.

As used herein, a $C_1$-$C_4$ alkylthio group is a said $C_1$-$C_4$ alkyl group, for example a $C_1$-$C_2$ alkyl group, which is attached to a sulphur atom.

As used herein, a $C_1$-$C_4$ alkylsulphinyl group is a said $C_1$-$C_4$ alkyl group, for example a $C_1$-$C_2$ alkyl group, which is attached to a S(=O) group.

As used herein, a $C_1$-$C_4$ alkylsulphonyl group is a said $C_1$-$C_4$ alkyl group, for example a $C_1$-$C_2$ alkyl group, which is attached to a S(=O)$_2$ group.

As used herein, the term $C_3$-$C_8$ cycloalkyl group denotes a saturated or unsaturated group. Preferably, the $C_3$-$C_8$ cycloalkyl group is saturated. Examples of $C_3$-$C_8$ cycloalkyl groups include cyclopropyl, cyclobutyl, cyclopentyl, cyclohexyl, cycloheptyl and cyclooctyl. Preferably, the $C_3$-$C_8$ cycloalkyl group is a cyclohexyl group.

As used herein, the term $C_2$-$C_6$ alkenyl refers to groups containing one or more carbon-carbon double bonds, which group may be straight or branched. Preferably, the $C_2$-$C_6$ alkenyl group is a $C_2$-$C_4$ alkenyl group. More preferably, the $C_2$-$C_6$ alkenyl group is a vinyl, allyl or crotyl group, most preferably an allyl group.

As used herein, the term $C_2$-$C_6$ alkynyl refers to groups containing one or more carbon-carbon triple bonds, which may be straight or branched.

Preferably, $R_1$ represents a straight or branched $C_1$-$C_6$ alkyl group or $C_2$-$C_6$ alkenyl group, which $C_1$-$C_6$ alkyl or $C_2$-$C_6$ alkenyl group is unsubstituted or substituted with 1 or 2 substituents selected from halogen (preferably chlorine, fluorine and bromine) atoms, $C_1$-$C_2$ alkoxy groups, preferably methoxy groups, and phenyl groups, which phenyl groups are unsubstituted or substituted with one or two substituents selected from $C_1$-$C_4$ alkoxy groups, preferably methoxy groups; or $R_1$ represents a cyclohexyl group.

More preferably, $R_1$ represents a straight or branched $C_1$-$C_6$, preferably $C_1$-$C_3$, alkyl group, said alkyl group being unsubstituted or substituted by a halogen (preferably chlorine or fluorine) atom.

Even more preferably, $R_1$ represents methyl or 2-haloalkyl, e.g. 2-fluoroethyl or 2-chloroethyl.

Most preferably, $R_1$ is methyl. Thus, the compound of formula (III) is typically methyl isocyanate (MIC).

Preferably, $R_3$ and $R_4$ are the same or different and are selected from hydrogen atoms and $C_1$-$C_4$ alkyl groups.

More preferably, one or both of $R_3$ and $R_4$ is hydrogen.

Typically, $R_3$ and $R_4$ are the same and are both hydrogen atoms. Thus, the compound of formula (II) is typically 5-diazo-5H-imidazole-4-carboxamide.

Preferably, $R_1$ is methyl and $R_3$ and $R_4$ are the same and are both hydrogen atoms. Thus, the compound of formula (I) is preferably temozolomide (TMZ).

Typically, the solvent used in the process of the present invention is an organic solvent. Those of skill in the art will easily be able to select appropriate organic solvents. Preferably, the solvent used is acetonitrile, toluene, diethyl ether, diisopropyl ether, methylisobutyl ketone, tetrahydrofuran or dioxane. More preferably, the solvent used is toluene, diethyl ether, diisopropyl ether, methylisobutyl ketone, tetrahydrofuran or dioxane. Even more preferably, the solvent used is tetrahydrofuran or dioxane.

In a preferred embodiment of the invention, the solvent used is dioxane, for example 1,2-dioxane, 1,3-dioxane or 1,4-dioxane. Most preferably, the solvent used is 1,4-dioxane.

Typically, the solvent used is substantially free of water. Methods of removing water from solvents are well known to those of skill in the art and include, for example, distillation or treatment with molecular sieves.

Typically, step i) comprises (a) providing a compound of formula (III) in gaseous form, preferably vapour form, and (b) condensing the compound of formula (III). Thus, steps i) and ii) together typically comprise (a) providing a compound of formula (III) in gaseous form, preferably vapour form, and (b) condensing the compound of formula (III) into the solvent. The compound of formula (III) is typically provided as a condensed vapour.

In certain embodiments, the compound of formula (III) may be provided in gaseous form, preferably in vapour form. Typically, said vapour comprises a compound of formula (III) in gaseous form, and an amount of the compound of formula (III) in liquid form (i.e. droplets).

Preferably, step i) comprises pyrrolysing N'-methyl-N,N-diphenyl urea. More preferably, in step i), a condensed vapour of methyl isocyanate is obtained by pyrrolysing N'-methyl-N,N-diphenyl urea and condensing the MIC vapours produced.

Typically, step (i) is carried out using processes known in the art, for example as described in U.S. Pat. No. 4,141,913, U.S. Pat. No. 4,207,251, U.S. Pat. No. 4,255,350, Japanese patent JP 56/100751, U.S. Pat. No. 4,391,758, U.S. Pat. No. 4,620,030 or U.S. Pat. No. 4,082,787, the entirety of which are incorporated herein by reference.

Typically; the pyrolysis of N'-methyl-N,N-diphenyl urea takes place at a temperature of from 200 to 300° C., preferably 260 to 280° C.

Typically, the pyrolysis of N'-methyl-N,N-diphenyl urea takes place over a period of from 1 to 5 hours, preferably 1.5 to 2.5 hours, more preferably 2 hours.

Typically, the vapours generated of compound formula III are condensed and absorbed in a suitable solvent N'-methyl-N,N-diphenyl urea is commercially available or can be prepared by well-known methods in the art, for example by reacting diphenylcarbamoyl chloride with aqueous monomethylamine. Diphenylcarbamoyl chloride and aqueous monomethylamine are commercially available or can be prepared by well-known methods in the art.

The skilled person will appreciate that the compound of formula (II) depicted herein embraces all tautomeric forms.

Typically, after addition of a compound of formula (II) in step iii) the mixture is maintained at a temperature of from 35 to 90° C., preferably 40 to 60° C., more preferably for from 6 to 24 hours, preferably 6 to 20 hours, more preferably 15 to 18 hours. Typically, this mixture is stirred.

Typically, after addition of a compound of formula (II) in step iii) the reaction is allowed to proceed until the amount of the compound of formula (II) present in the reaction mixture determined by HPLC analysis is <0.5%.

Typically, the molar ratio of the compound of formula (III) to the compound of formula (II) is typically 1.8:1 to 5:1, preferably 2:1 to 2.4:1.

Typically, the ratio of the solvent in which the compound of formula (III) is dissolved to compound of formula (II) is from 2:1 to 10:1, more preferably 4:1 to 6:1.

Typically, an excess of compound of formula (III) is used compared to compound of formula (II).

Typically, between steps (ii) and (iii) the content of compound of formula (III) present in the solvent is calculated using known methods, for example the method described in Analyst, 1999, vol. 124, (9), 1327-1330.

Compounds of formula (II) used in the present invention can be prepared by application or adaptation of known methods, for example as described in Journal of Organic Chemistry (1961), 26, 2396. The reaction as described in the above-referenced article is typically carried out in an aqueous or organic solution with a source of nitrous acid. The reaction as described in the above-referenced article is typically conducted in water or in organic solvents like Tetrahydrofuran (THF), ethyl acetate or acetone. The reaction can also be conducted with an organic source of nitrous acid eg t-butyl or isopentyl nitrite with a carboxylic acid such as lower alkanoic $C_{1-6}$ acid, e.g. acetic acid.

Typically, the process of the present invention takes place in a closed system. This minimises the risk of exposure/release to the environment.

Typically, in step iv), any excess compound (III) remaining after the reaction has gone substantially to completion is decomposed by treating with aqueous acid. This allows safe disposal of any remaining isocyanate, e.g. MIC.

In a preferred embodiment, step iv) comprises treating with aqueous acid to decompose excess compound (III) and further comprises the salification (i.e. salt preparation) step v).

Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid.

Pharmaceutically acceptable bases are typically metal hydroxides, preferably alkali metal hydroxides, for example sodium or potassium hydroxide.

Preferably, step v) comprises salifying the thus obtained compound with a pharmaceutically acceptable acid.

Typically, after step v), the compound of formula (I) is isolated. Typically, isolation of the compound of formula (I) is effected by adding ethyl acetate to the reaction mixture and removing the crude product by filtration. The filtered product is typically washed with ethyl acetate.

Typically, the crude product is then purified by slurrying in acetone, or acetone-water (3:1) and crude compound of formula (I) removed by filtration. The pH of water used in the acetone-water mix is typically adjusted between 4-4.5 with acetic acid.

When the compound of formula (I) is temozolomide, the overall yield of crude product is typically 50-86%. The crude TMZ obtained typically has a purity of 98 to 99.5%, preferably greater than 99% (e.g. 99.2-99.5%).

The crude compound of formula (I) obtained is then typically purified further by recrystalising from acetone-water. The acetone-water used typically has an acetone water ratio from 1:0.3 to 1:5, preferably 1:0.3 to 1:3, by volume.

When the compound of formula (I) is temozolomide, the overall yield of recrystallised product is typically 35-63%. The purity of the recrystallised product is typically 99.8 to 99.9% or may be, for example, greater than 99.9%. Typically, impurity levels are below 0.1% as compared to 0.15% achieved in the process of the prior art.

When the compound of formula (I) is Temozolamide, the recrystallised product obtained in the above manner has a purity not less than 99.9% and contains less than 0.1% of 5-diazo-5H-imidazole-4 carboxamide or 5-aminoimidazole-4-carboxamide.

As noted above, in a preferred embodiment of the invention, the solvent is dioxane. It is a finding of the invention that an MIC-dioxane mixture is the most suitable. Thus, MIC was absorbed in various solvents such as tetrohydrofuran (THF), methylisobutyl ketone (MIBK), diethyl ether, diisopropyl ether, toluene, acetonitrile and DMSO etc. Reactions were carried out between the solutions prepared and 5-diazo-51'-imidazole-4 carboxamide. It was found out that an MIC-dioxane mixture is the most suitable as the reaction proceeded to completion in 6-20 hours. In most other solvents, reaction did not occur or did not go to completion. Also being a water-miscible solvent, the down stream processing of MIC is easier in dioxane compared to other conventional solvents.

The present invention provides an efficient method of handling MIC, wherein the condensed MIC vapours are absorbed into a suitable solvent. Exposure hazards associated with MIC can be reduced greatly compared with processes described in the prior art.

The present invention provides a faster reaction of 5-diazo-5H-imidazole-4 carboxamide with methyl isocyanate. The reaction rate is enhanced as the MIC is present in a suitable solvent and, further, exposure to excess vapours is minimised. Further, excess MIC in the solution after the reaction is then destroyed using acidic water. All the steps of the reaction are typically carried out in closed condition, thus avoiding exposure to MIC.

The process of the present invention is a convenient process for the preparation of Temozolomide with a high yield and purity using better preparation techniques that are safe, cost-effective, robust and well suited for industrial use. The process is simple, efficient, industrially feasible and ecofriendly.

EXAMPLES

The following Examples are included to demonstrate preferred embodiments of the invention. It should be appreciated by those of skill in the art that the techniques disclosed in the Examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of 5-diazo-5H-imidazole-4 carboxamide 47 g of sodium nitrite was dissolved in 1.2 liters of water and the solution cooled to 0° C. 100 g of 5-aminoimidazole-4 carboxamide was dissolved in a solution of hydrochloric acid (80 ml of 36% HCL in 720 ml water) with stirring, and the resultant 5-aminoimidazole-4 carboxamide hydrochloride solution was added slowly, drop-wise over a period of 20-30 minutes at 0-5° C.

After the addition was completed, the reaction mixture was stirred for 10 minutes and filtered. The solid obtained was suspended in 400 ml DM water and stirred for 15 minutes. The suspension was filtered and suction dried for 15 mins. The obtained solid was suspended in 500 ml of THF and stirred for 15 minutes. The suspension was filtered and suction dried for 15 minutes. Finally, the solid was dried at 45° C. to afford 60 gms of the title compound. Purity: 96.4% by HPLC.

Example 2

Preparation of MIC 60 g of N'-Methyl-N,N-diphenyl urea was charged into a clean and dry round bottomed flask equipped with a condenser and a receiver charged with 60 ml of 1,4-dioxane. The round bottom flask containing N'-Methyl-N,N-diphenyl urea was heated to 260-280° C. for a period of 2 hours and condensed vapours comprising methyl isocyanate were absorbed in the receiver containing Dioxane. Estimation of MIC content was carried out as per the method described in Analyst, 1999, vol 124, (9), 1327-1330. The MIC content was found to be 16% w/w.

Example 3

Preparation of TMZ 15 g of 5-diazo-5H-imidazole-4 carboxamide was added to the flask containing methyl isocyanate absorbed in dioxane obtained in Example 2. The reaction mass was then heated to 50° C. and the temperature maintained for 15-18 hours until HPLC showed that the starting material had been consumed. The reaction mixture was then cooled to 30° C. and 8 ml of acidic water was added.

The reaction mixture was stirred for 30 minutes. 60 ml of Ethyl acetate was added. The reaction mixture was stirred for 60 minutes and filtered. The solid obtained was washed with 15 ml of ethyl acetate and suction dried for 15 minutes. The solid was suspended in 45 ml of acetone and stirred for 30 minutes. The solid was filtered and suction dried for 15 minutes. The yield was 18 g with a moisture content of 1%. The corrected yield is 16.5 g (78.5%) with a purity of 99.74%.

Example 4

Study on the Rate of Reaction Using Various Solvents

Experiments were carried out as in Example 3 using various solvents and temperatures. The yields of temozolomide and the amount of unreacted diazo compound remaining are show in the table below.

| Solvent | Temozolomide | Unreacted Diazo | Temperature of reaction for 24 hrs |
|---|---|---|---|
| Acetonitrile | Less than 1% | 99% | 25-30° C. |
| Toluene | 6% | 94% | 25-30° C. |
| Disopropyl ether | 7% | 93% | 50° C. |
| Methylisobutyl ketone | 16% | 84% | 50° C. |
| Tetrahydro furan | 70% | 27% | 50° C. |
| Dioxane | 66% | 32% | 25° C. |
| Dioxane | 99.74% | 0.21% | 50° C. |

These results clearly show that the best yield and purity of temozolomide can be obtained using a dioxane solvent and a temperature of 50° C.

Example 5

Purification of Temozolomide 900 ml of a mixture of Acetone-water (3:1 respectively by volume) were charged into a round bottomed flask. A wet cake of crude product obtained in above Example 3 (moisture 1%, LOD 9%) was added and the mass was heated to 50° C. to dissolve temozolomide. After complete dissolution, 1.5 g acidic charcoal was added and the mixture stirred for 30 minutes. The mixture was filtered over a celite bed and washed with 30 ml acetone. The solution was cooled slowly to 0° C. and maintained at that temperature for 60 minutes. The obtained suspension was filtered and the solid slurry washed with 60 ml of acetone. The solid was filtered and suction dried for 15 minutes. The wet cake was then dried under vacuum to yield 12 g (57%) of Temozolomide. Purity: 99.9% by HPLC.

Analysis of Impurities and Yields by HPLC

HPLC analysis was performed using a gradient method using Inertsil ODS, 3.0 V (250×4.6 mm), 5.0μ column. The details are as tabulated below:

Related Substance by HPLC

Reagents and Glassware

| No. | Name | Grade |
|---|---|---|
| 1 | Water | Mili 'Q' water |
| 2 | Methanol | HPLC grade |
| 3 | Glacial Acetic acid | Analytical reagent grade |
| 4 | Volumetric flask | Class A |

Chromatographic System:

| 1 | Mobile phase | A:B (Gradient) |
| 2 | Mobile phase A | 5.0 ml of glacial acetic acid in 1000.0 ml water. |
| 3 | Mobile phase B | Methanol |
| 4 | Column | Inertsil ODS, 3.0 V (250 × 4.6 mm), 5.0μ |
| 5 | Wavelength | 254 nm |
| 6 | Flow rate | 1.0 ml/min |
| 7 | Column temperature | 25° C. |
| 9 | Diluent | MP A:MP B (90:10 v/v) |
| 10 | Run time | 60.0 min |
| 11 | Injection volume | 10.0 μl |
| 12 | Sample compartment temperature | 5.0° C. |

Gradient Program

| Time (Min) | Mobile phase A % | Mobile phase B % |
|---|---|---|
| 0.0 | 90 | 10 |
| 8.0 | 90 | 10 |
| 25.0 | 50 | 50 |
| 40.0 | 20 | 80 |
| 50.0 | 10 | 90 |
| 55.0 | 90 | 10 |
| 60.0 | 90 | 10 |

Samples of temozolomide and expected impurities were analysed by HPLC using the above-described method and the retention times noted. Relative retention times were calculated. The impurities, retention times and relative retention times of the five samples tested are detailed in the table below.

| No. | Name | Aprox. Retention time (min) | RRT |
|---|---|---|---|
| 1 | 5-Aminoimidazole-4-carboxamide hydrochloride (Imp-1) | 2.1 | 0.21 |
| 2 | 5-Diazo-5H-imidazole-4-carboxyic acid amide (Imp-2) | 6.4 | 0.63 |
| 3 | Temozolomide | 10.2 | 1.0 |
| 4 | N-Methyl-N,N-diphenyl urea (Imp-3) | 35.2 | 3.45 |
| 5 | Diphenyl carbomyl chloride (Imp-4) | 42.3 | 4.15 |

A sample of Temozolomide prepared according to the process of the present invention was then analysed by HPLC using the same method. The amounts of known and unknown impurities were then calculated using the equations detailed below.

$$\% \text{ Known Impurity} = \frac{AK \times DS \times P}{AS \times DT \times RRF}$$

$$\% \text{ Unknown Impurity} = \frac{AU \times DS \times P}{AS \times DT \times RRF}$$

Total Impurities=Known Impurities+Unknown impurities.

AK=Area of known impurity in the chromatogram of the sample solution

AS=Mean area of Temozolomide in the chromatogram of the reference solution

AU=Area of unknown impurity in the chromatogram of the sample solution

DU=Dilution factor of known impurity in sample solution

The results obtained for the sample of Temozolomide tested are given in the box below.

| | |
|---|---|
| 5-aminoimidazole-4-carboxamide | 0.02% |
| diphenyl carbomoyl chloride | not detected |
| N'-methyl-N,N-diphenyl urea | not detected |
| 5-diazo-5H-imidazole-4 carboxamide | not detected |
| Unidentified impurities | 0.06% |

Thus, it can be seen that Temozolomide prepared in accordance with the present invention has an extremely high level of purity (99.9%).

Comparative Example 1

A comparison (in terms of yield) of the process of the present invention and the process described in US-A-2007/0225496 was made. The results are present in the table below.

| Reaction step | Process as described in US-A-2007/0225496 (yield (w/w) %) | Process of the present invention (yield (w/w) %) |
|---|---|---|
| 5-aminoimidazole-4 carboxamide to 5-diazo-5 H-imidazole-4 carboxamide | (0.54), 64% | (0.66), 78.5% |
| 5-diazo-5 H-imidazole-4 carboxamide to temozolamide (crude) | (0.96), 68.6% | (1.1), 78.5% |
| 5-diazo-5 H-imidazole-4 carboxamide to temozolamide (pure) | (0.577), 41% | (0.88), 62.8% |

Thus, while we have described fundamental novel features of the invention, it will be understood that various omissions and substitutions and changes in the form and details may be possible without departing from the spirit of the invention. For example, it is expressly intended that all combinations of those elements and/or method steps, which perform substantially the same function in substantially the same way to achieve the same results, be within the scope of the invention.

The invention claimed is:

1. A process for the preparation of temozolomide, or a pharmaceutically acceptable salt thereof, comprising:
   i) pyrrolysing N'-methyl-N,N-diphenyl urea and obtaining a condensed vapor form of methyl isocyanate;
   ii) condensing the vapor form of the methyl isocyanate to obtain a solution of the methyl isocyanate;
   iii) adding to the thus obtained solution a compound of formula (II),

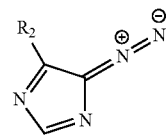

wherein $R_2$ represents a group of formula —(C=O)$NR_3R_4$, wherein $R_3$ and $R_4$ are the same and are both hydrogen atoms,
   iv) decomposing any excess of the methyl isocyanate remaining by addition of water to obtain temozolomide, and
   v) optionally salifying the temozolomide with a pharmaceutically acceptable acid, or base.

2. A process according to claim 1, wherein the solvent is dioxane.

3. A process according to claim 1, wherein the pyrrolysis of N'-methyl-N,N-diphenyl urea in step (i) takes place for 1 to 5 hours.

4. A process according to claim 1, wherein the pyrrolysis of N'-methyl-N,N-diphenyl urea in step (i) takes place at a temperature of from 200 to 300° C.

5. A process according to claim 1, wherein the reaction mixture obtained in step (iii) is maintained at 35 to 90° C. for 6 to 24 hours.

6. A process according to claim 1, wherein the molar ratio of methyl isocyanate to the compound of formula (II) is from 1.8:1 to 5:1.

7. A process according to claim 1, wherein the ratio of the solvent in which the methyl isocyanate is dissolved to the compound of formula (II) is from 2:1 to 10:1.

* * * * *